United States Patent [19]
McAteer et al.

[11] Patent Number: 6,118,003
[45] Date of Patent: Sep. 12, 2000

[54] PROCESSES FOR PRODUCING 3-CYANOPYRIDINE FROM 2-METHYL-1,5-PENTANEDIAMINE

[75] Inventors: Colin H. McAteer, Indianapolis; Joel R. Calvin, Carmel; Robert D. Davis, Sr., Greencastle, all of Ind.

[73] Assignee: Reilly Industries, Inc., Indianapolis, Ind.

[21] Appl. No.: 09/015,831

[22] Filed: Jan. 29, 1998

[51] Int. Cl.⁷ .................. C07D 213/09; C07D 213/133; C07D 213/16; C07D 213/127; C07D 213/85

[52] U.S. Cl. .............................................. 546/286

[58] Field of Search .............................. 546/286

[56] References Cited

U.S. PATENT DOCUMENTS

| | | | |
|---|---|---|---|
| 3,555,021 | 1/1971 | Beutel et al. | 260/250 |
| 4,051,140 | 9/1977 | Gelbein et al. | 260/290 P |
| 4,086,237 | 4/1978 | Daum et al. | 260/290 P |
| 4,401,819 | 8/1983 | Cordier et al. | 546/252 |
| 4,603,207 | 7/1986 | DiCosimo et al. | 546/286 |
| 4,876,348 | 10/1989 | DiCosimo et al. | 546/251 |
| 5,028,713 | 7/1991 | DiCosimo et al. | 546/286 |

FOREIGN PATENT DOCUMENTS

| | | |
|---|---|---|
| 7005792 | 4/1970 | Netherlands . |
| 755534 | 12/1953 | United Kingdom . |
| 2165844A | 4/1986 | United Kingdom . |

OTHER PUBLICATIONS

Thomas, C.L., "Chapter 2: Buring Coke Off Catalysts", *Catalytic Processes and Proven Catalysts*, Academic Press (1970), pp. 11–14.

Bailey, T.D., Goe, G.L. and Scriven, *Pyridine and Its Derivatives, Part Five*, pp. 106–252, 1984.

*Pyridine and Its Derivatives, Part One*, Interscience Publishers (1960), pp. 272–354.

*Primary Examiner*—Floyd D. Higel
*Attorney, Agent, or Firm*—Woodard, Emhardt, Naughton Moriarty & McNett

[57] ABSTRACT

A process for the production of 3-cyanopyridine by ammoxidation of 2-methyl-1,5-pentanediamine to form 3-cyanopyridine, optionally carried out as an oxidative ammonolysis process.

25 Claims, No Drawings

PROCESSES FOR PRODUCING 3-CYANOPYRIDINE FROM 2-METHYL-1,5-PENTANEDIAMINE

BACKGROUND OF THE INVENTION

The present invention relates generally to the production of 3-cyanopyridine and in particular to a process which involves the direct ammoxidation of 2-methyl-1,5-pentanediamine, alone or in admixture with 3-methylpiperidine, to 3-cyanopyridine.

As further background, the manufacture of 3-cyanopyridine and other pyridine derivatives has been and continues to be of major commercial interest on a variety of fronts. For example, 3-cyanopyridine is an intermediate to a large number of agricultural and pharmaceutical products. A number of known processes for preparing 3-cyanopyridine and other pyridine derivatives involve catalytic cyclization and dehydrogenation reactions. Many such reactions are reviewed by Brody and Ruby in Volume 1 of *Pyridine and Its Derivatives*, E. Klingsberg, ed., and most recently by Bailey, Goe and Scriven, in Vol. 5 of the *Supplement to Pyridine and Its Derivatives*, G. C. Newkome, ed. These reactions have generally been carried out in the gas phase at low to moderate temperatures up to about 400° C. using predominantly precious metal catalysts such as palladium and platinum.

For example, British Patent No. 755,534 issued in 1956 to ICI describes the conversion of pentanediamine (PDA) to pyridine in 55% yield using a catalyst of 5% platinum on a silica support at 400° C. This patent also reports the conversion of PDA to piperidine using acidic heterogeneous catalysts such as silica, silica-alumina beads and boron phosphate, without the precious metal or any other metal component at 350° C. Other examples include the following:

Netherlands patent application No. 7,005,792 (Deumens, Groen, and Lipsch, 1971 to Stamicarbon; Chem. Abstr., 76, 46099) reports converting PDA to piperidine in high yield using a catalyst of Raney-nickel supported on silica or to various mixtures of piperidine an d pyridine using a catalyst of palladium supported on alumina at 125–300° C.

U.S. Pat. No. 4,086,237 issued in 1978 to Dynamit Nobel (equivalent to German Patent No. 2,519,529) reports the conversion of 2-methyl-1,5-pentanediamine alone or with 3-methylpiperidine to mostly 3-methylpyridine using palladium metal on an alumina support at 200–400° C. U.S. Pat. No. 4,401,819 issued in 1983 to Rhone-Poulenc reports a similar conversion using a precious metal on a particular macroporous solid silica support at 200–500° C.

British patent application No. 2,165,844 filed in 1986 by ICI reports the eventual conversion of glutaronitrile to pyridine, perhaps with the preferred isolation of 1,5-pentanediamine as an intermediate, using palladium metal on silica support at 350–400° C.

Collectively, these references show that pentanediamine and its alkyl derivatives have been selectively converted in the past to their piperidine counterparts using catalyst supports alone or in combination with the Group VIII metal, or to admixtures of these piperidines and their pyridine counterparts using various Group VIII precious metals (also called noble metals) including palladium and platinum at temperatures of about 400° C.

Specifically with regard to the ultimate preparation of cyanopyridines, this cyclization and dehydrogenation work has suffered since in large part it has focused upon the production of methylpyridines, which must be converted in subsequent manipulations to cyanopyridines. U.S. Pat. No. 5,028,713 does disclose the conversion of 2-methylglutaronitrile to 3-cyanopyridine. However, both the reported yields and those obtained in the applicants' comparative work set forth in the Examples below are extremely low, making this process unattractive for commercial scale production.

Thus, especially with respect to cyanopyridines, there has been a growing need and economic driving force for an improved route to cyanopyridines starting with methyl-1,5-pentanediamines. The present invention is addressed to this need.

SUMMARY OF THE INVENTION

In particular, the applicants, through their work in this field, have made the surprising and significant discovery that methyl-1,5-pentanediamines such as 2-methyl-1,5-pentanediamine, can be converted via an ammoxidation process directly to their cyanopyridine counterparts (e.g. 3-cyanopyridine) in significant yields. Accordingly, the present invention provides in one preferred embodiment a process for preparing 3-cyanopyridine which comprises an ammoxidation of 2-methyl-1,5-pentanediamine directly to 3-cyanopyridine. Preferred temperatures for the ammoxidation range from about 300° C. to about 500° C., more preferably about 350° C. to about 450° C. Preferred catalysts include vanadium and/or precious metal catalysts. In addition, the 2-methyl-1,5-pentanediamine starting material can be used alone or admixed with 3-methylpiperidine, as in the hydrogenation products of 2-methylglutaronitrile (MGN).

One embodiment of this process utilizes a fluid-bed reactor for efficiency and ease of operation including separation and recovery of the 3-cyanopyridine product. In other embodiments, the vanadium or other metal catalysts are supported on a suitable heterogeneous support such as silica, alumina or a combination thereof as in an amorphous or a crystalline zeolite form.

In another embodiment of the invention, the ammoxidation process is conducted as an oxidative ammonolyisis process. In such process a methyl-1,5-pentanediamine such as 2-methyl-1,5-pentanediamine is reacted with ammonia in a first reactor in the presence of an oxygenated catalyst, e.g. a vanadium or precious metal catalyst, and the reaction product containing 3-cyanopyridine is recovered while the oxygen-depleted catalyst is fed to a second reactor and regenerated in the presence of oxygen. The regenerated catalyst is then transferred to the first reactor in order to complete the catalytic cycle. An alternative approach to moving catalyst between two or more reactors is to maintain the catalyst in a single reactor and use alternate feed cycles of the methyl-1,5-pentanediamine-ammonia mixture and then an oxygen-containing gas.

Additional objects and advantages of the present invention will be apparent from the following description.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the invention and such further applications of the principles of the invention as described herein being contemplated as would normally occur to one skilled in the art to which the invention relates.

As stated above, the applicants have discovered that 2-methyl-1,5-pentanediamine is readily converted to 3-cyanopyridine by ammoxidation in the presence of a catalyst. This contacting step (and resulting reaction) takes place at a temperature of about 300–500° C., and preferably over a contact time of less than about 30 seconds. In addition, oxidative ammonolysis processes can also be conducted starting with 2-methyl-1,5-pentanediamine, to produce 3-cyanopyridine. In such processes the 2-methyl-1,5-pentanediamine is contacted first with ammonia in the presence of the catalyst to form 3-cyanopyridine in a first reaction zone at a temperature of about 300° C. to about 500° C., and then the resulting oxygen-depleted catalyst is fed to a second reaction zone where it is contacted with an oxygen-containing gas at a temperature of about 300° C. to about 550° C.

It is contemplated that effective catalysts for these reactions include both supported and unsupported forms. It will be appreciated, however, that catalysts supported on a suitable heterogeneous support such as silica, alumina or silica-alumina in some form can be an economic advantage particularly in a fluid-bed operation.

The most effective and preferred catalysts to date have comprised supported vanadium oxides. It will be understood, however, that a wide variety of catalysts are contemplated as being suitable for the present invention, including for example precious metal catalysts such as platinum and palladium catalysts, as well as molybdenum oxide and/or copper-chromite catalysts (each potentially on a wide variety of supports).

The use of the term "effective" relates to the ability of a catalyst to enhance the production of the desired 3-cyanopyridine product under the reaction steps and conditions as defined herein. Various of the experimental results achieved by the applicants to date are set forth in the specific Examples and Tables below. However, in view of the number of variables present, a variety of other catalysts may also be found to be effective in the production of 3-cyanopyridine under conditions such as those described herein, and will also form a part of the present invention. Preferably, the reaction undertaken will approach a yield of about 20% or more 3-cyanopyridine based on a conversion approaching 100% of the original organic feed stream.

Catalysts useful in the present invention can be obtained commercially and/or prepared by methods well known to the art and literature. For example, for a supported metal oxide catalyst, a salt that is soluble in water can be absorbed on the desired support and then decomposed to the desired oxide by heat (also known as calcining). An alternative method is to form the desired metal oxide as an ion-exchanged form of a zeolite, and then to calcine the resulting zeolite salt to form the desired catalyst. These and other methods known to those of ordinary skill in this art can be used in preparing catalysts used in the present invention. Regardless of their source, these catalysts can be prepared or purchased in many usable sizes and shapes such as pellets, extrusions or spheres for fixed-bed use or as powders or microspheroidal materials for fluid-bed use. These and other physical factors involved in catalyst selection, preparation and handling vary with the specific equipment, conditions and reaction selected, and are well within the ordinary skill of those in this field.

The applicants' reactions are preferably carried out in the usual fashion of continuous gas-phase reactions of this type, in which the reactants are vaporized and this feed stream then passed in contact with the catalyst which is maintained at the desired temperature. In this way, the vaporized reactants are conducted over the catalyst to produce a suitable contact time for the reaction to take place. This contact time may be seen as the time required to achieve a desired or maximum conversion which is often expressed as a percentage of the original reactants passed. The preferred contact time in a particular reaction must be found by trial and error under the specific circumstances involved, unless prior comparative data is available.

Contact times of about 30 seconds or less will be preferred in the present invention, more preferably about 10 seconds or less. Significantly longer contact times may require specially designed equipment, and can result in product decomposition or other unwanted by-products at the elevated temperatures involved.

Generally, ammoxidation reactions in accordance with the present invention will desirably be carried out at a temperature in the range of about 300–500° C., more preferably about 350–450° C. In specific work, temperatures in the range of about 400° C. have provided good results. It will be understood, nonetheless, that each reaction must be examined on its own to determine optimum conditions, including temperature, under given circumstances.

As indicated above, ammoxidation processes of the invention can optionally be carried out as "oxidative ammonolysis processes", in which the ammonia and 2-methyl-1,5-pentanediamine (with no or a reduced level of gaseous oxygen feed) are passed over the catalyst bed after pre-oxygenation of the catalyst bed. Such oxidative ammonlysis reactions of the invention are preferably carried out at temperature of about 350° C. to about 450° C. for the 3-cyanopyridine forming step, and about 450° C. to about 550° C. for the catalyst regeneration (oxygenation) step. Again, however, each reaction step will be examined on its own to determine optimum conditions, as those skilled in the art will understand. In addition, for further information as to oxidative ammonolysis reactions in general, reference can be made to U.S. Pat. No. 4,051,140.

The ammoxidation and oxidative ammonolysis reactions of the invention may be carried out in fixed-bed or fluid-bed operations. Fixed-bed reactors in this field are well documented both in practice and in the literature. The same is true of fluid-bed reactors, although more variables exist. For example, the feed rates of the vapor reactants are chosen to give sufficient fluidization of the catalyst bed. These are usually at a superficial velocity between about 0.08 m/sec and 1.2 m/sec, although lower or higher velocities may be chosen in given circumstances. The reaction products are collected by condensation and individual products are separated and recovered as desired, frequently by distillation means. If the process yields a mixture of the piperidine and pyridine derivatives, one alternative is to subject the mixture to further catalytic reaction to dehydrogenate the remaining piperidine material. Another alternative is to first isolate the pyridine product and then to recycle only the piperidine component back through the reactor. In any case, the general construction and operation of a fluid-bed or a fixed-bed reactor are no different for the applicants' processes than for other reactions for which they are used. Reference can thus be made to available literature or other sources in this area as to the specific establishment and operation of such reactors, the same being well within the skill of those practiced in this art.

As for the starting materials used, the reaction zone in applicants' preferred ammoxidation processes needs only to contain ammonia, an oxygen source (e.g. a feed of oxygen gas), and an amount of 2-methyl-1,5-pentanediamine. For amoxidation processes which involve oxidative ammonolysis reactions, the first stream will contain these same materials except no feed of oxygen gas is used or less oxygen gas is used, and except for regeneration of the catalyst in the presence of oxygen in the second reaction zone. In either case, the initial reactant stream is vaporized and passed in contact with the heated catalyst bed to bring about the reaction. As for ratios of these reactants, preferred ammonia to organic (e.g. 2-methyl- 1,5-pentanediamine alone or together with 3-methylpiperidine) molar ratios are at least about 1:1, more preferably at least about 2:1. Preferred oxygen to organic molar ratios will be at least about 3:1, more preferably about 3:1 to about 10:1. When air is used as the oxygen source, this corresponds to an air to organic molar ratio of about 15:1 to about 50:1. Of course if desired, the air, when used in the present invention, can be depleted or enriched in certain components, e.g. nitrogen-depleted. Other materials may also be present in the feed stream as long as they do not interfere significantly with the production of 3-cyanopyridine, including for example 3-methylpiperidine, water, or inert gases.

A recognized problem with catalysts in this area has been that their activities gradually decrease over time due in part to the build up of carbonaceous deposits. With most catalysts regeneration is possible, for example, by heating in the presence of air or some other oxygen-containing gas. See Charles L. Thomas, *Catalytic Processes and Proven Catalysts*, pp. 11–14 (1970). This may be followed by passing hydrogen over the hot catalyst before returning it to contact with a further reactant stream. This need for periodic regeneration encourages the use of fluid beds for such reactions, which beds are capable of being regenerated either in total at certain intervals or in part by the catalyst being continuously or intermittently circulated to a second reaction vessel in which regeneration takes place. Such reactors are commonly used in industry for reactions such as the catalytic cracking of petroleum and in pyridine synthesis.

While the invention has been described in detail in the foregoing paragraphs, the same is to be considered as illustrative and not restrictive in character. It is understood that only the preferred embodiments have been described and that all changes and modifications that come within the spirit of the invention are desired to be protected.

In this regard, some specific Examples and Tables follow which reflect experimental runs performed by the applicants using their catalysts and processes described above. In these, reference is made to 2-methyl-1,5-pentanediamine as "2-MePDA", to 3-methylpiperidine as "3-MePip", to 3-cyanopyridine as "3-CN" and to beta-picoline as "β-pic". Conversions, or "X", are expressed as a percentage calculated by dividing moles of organic compound reacted by moles of organic compound fed into the reactor in the feed stream. Yield, or "Y" is expressed as a percentage calculated by dividing moles of specific product obtained (e.g. $Y^{3-CN}$ or $Y^{\beta-pic}$) by moles of organic compound fed into the reactor in the feed stream. Total yield, or "$Y^{Tot}$" is expressed as the sum of $Y^{3-CN}$ and $Y^{\beta-pic}$. Selectivity, or "S", is expressed as a percentage calculated by dividing moles of specific product obtained (e.g. $S^{3-CN}$ or $S^{\beta-pic}$) by moles of organic compound reacted.

EXAMPLE 1

Reactor and General Conditions

A fixed-bed quartz microreactor (I.D.=18 mm), fitted with a thermowell (O.D.=5 mm), was used to evaluate catalyst formulations. A catalyst bed volume of 4 mL was used with a particle size range of 0.25–0.50 mm. Two plugs of an inert ceramic wool were used at either end of the catalyst bed to secure its position within the reactor. The catalyst bed was positioned in the isothermal region of a 25 mm I.D. tube furnace. A syringe pump was used to deliver the liquid feed(s) to a stainless steel transfer line for vaporization directly into the catalyst bed. Gaseous feeds ($NH_3$, air) were individually metered using calibrated rotometers prior to mixing and delivery to the catalyst bed. The reaction contact time (CT) was calculated based on total moles of vaporized feed at the catalyst bed temperature. Constant ammonia/organics ($NH_3$/org) and air/organics (air/org) molar ratios were maintained throughout the runs (organics refers to the molar sum of each component in the case of mixed feeds).

The reactor effluent was directed into a pyrex condenser unit maintained at room temperature. Liquid products, containing dissolved 3-CN, were collected and weighed at predetermined time intervals with the mid-point being recorded as the hours-on-stream (HOS). The composition of the liquid effluent was determined by gas chromatography using an internal standard method.

EXAMPLE 2

Catalyst Preparations

A number of catalysts were prepared containing 10% w/w vanadia on oxide supports using an oxalic acid procedure. This involved reducing ammonium vanadate with excess oxalic acid in water at 70–90° C. The resulting vanadyl oxalate solution was added to the oxide support, either as a powder or as pre-sieved particles in the 0.25–0.50 mm size range, using a standard incipient wetness procedure. The resulting vanadium-loaded support was dried in an oven (70–90° C./10–20 hours) and then calcined at 550° C. for 6 hours. Where powders were used in the impregnation sequence, a further silica binding step was used to produce a solid cake (about 20% w/w $SiO_2$) from which crushing and sieving provided particles in the 0.25–0.50 mm size range. The silica binding procedure involved mixing the 10% vanadia powder with Ludox AS-40 (DuPont), drying the resulting paste and calcination.

A number of the oxide supports used were commercially available, e.g. zeolite-L (LTL), MOEC (an FCC catalyst formulation containing about 40% w/w $Al_2O_3$) and calcined hydrotalcite. Other oxides were prepared from the nitrate salts using standard precipitation (ammonium bicarbonate), drying and calcination techniques. The precipitation procedure was used to prepare $ZrO_2$, $La_2O_3$ and $CeO_2$ supports. A sample of anatase-$TiO_2$ was prepared by the simple addition of an isopropanol-[Ti(O$^i$Pr)$_4$] solution to water giving a precipitate which was filtered, water washed, dried and calcined (350° C./6 hours). A $SiO_2$—$Al_2O_3$ support, containing 50% w/w $Al_2O_3$, was prepared by ammonium bicarbonate precipitation of aluminum nitrate in the presence of Ludox AS-40.

The "VPO" catalyst was prepared by refluxing vanadia in $^iBuOH$—$PhCH_2OH$ solution (16 hours), adding $H_3PO_4$ and refluxing for a further hour. The recovered solid was dried (70° C./12 hours), calcined (450° C./6 hours) and then crushed and sieved to size.

The $V_2O_5/Sb_2O_3/TiO_2$ catalyst was prepared by intimate mixing (mortar and pestle) of the oxides in the following composition: $\{V_2O_5\}\{Sb_2O_3\}_4\{TiO_2\}_8$. The mixed powder was calcined at 500 C. for 3 hours, 650° C. for 1 hour and then 730° C. for 3 hours. The calcined powder was bound with 20% w/w $SiO_2$ (Ludox AS-40) as described above.

The $PVMo/SiO_2$ catalyst was prepared according to Example 2 of U.S. Pat. No. 4,876,348 assigned to The Standard Oil Company of Ohio.

EXAMPLE 3

Experimental Runs

A series of runs was performed to produce 3-CN from aqueous 2-MePDA using various catalysts prepared as described above, and the results and reaction conditions are shown in Table 1. Under the conditions employed, the 10% $V_2O_5$:45% $SiO_2$:45% $Al_2O_3$ gave the best results, although a variety of catalysts produced significant amounts of 3-CN.

Another series of reactions was performed similar to that reported in Table 1, except using a range of air/organic and $NH_3$/organic ratios and the Ludox-bound $V_2O_5$/MOEC catalyst. Table 2 shows the results, in which it is clear that higher $S^{3-CN}$ values were obtained at higher air/organic ratios. The highest $S^{3-CN}$ value observed was about 39% (Example 30) using a contact time of 2.9 seconds, a $NH_3$/organic ratio of ca. 13.0 and an air/organic ratio of about 28.0. This reaction also gave a relatively clean 3-CN product, with very little β-picoline present.

TABLE 1

Bed Volume = 4 mL; Particle Size = 0.25–0.50 mm
Feed = 50% w/w/ 2-MePDA in $H_2O$; Contact time = 1.1–1.6 sec
$NH_3$/Org = 6.2–7.1; Air/org = 13.9–18.1

| Ex | Catalyst | HOS | T/°C. | X | $S^{β-pic}$ | $S^{3-CN}$ | $S^{Tot}$ | $Y^{β-pic}$ | $Y^{3-CN}$ | $Y^{Tot}$ |
|---|---|---|---|---|---|---|---|---|---|---|
| 3A | $V_2O_5$/$Al_2O_3$—$SiO_2$ | 1.6 | 400 | 100 | 22 | 17 | 39 | 22 | 17 | 39 |
|    |    | 2.7 |     | 100 | 12 | 16 | 28 | 12 | 16 | 28 |
|    |    | 4.1 |     | 95  | 9  | 18 | 27 | 8  | 17 | 25 |
| 3B | $V_2O_5$/$ZrO_2$ | 1.5 | 410 | 99 | 20 | 1 | 21 | 20 | 1 | 21 |
|    |    | 2.5 |     | 99 | 20 | 0 | 20 | 19 | 0 | 19 |
|    |    | 4.1 |     | 99 | 19 | 0 | 19 | 19 | 0 | 19 |
| 3C | $V_2O_5$/$TiO_2$ | 1.6 | 430 | 92 | 16 | 9  | 25 | 14 | 8 | 22 |
|    |    | 2.6 |     | 86 | 16 | 10 | 26 | 14 | 8 | 22 |
|    |    | 3.8 |     | 82 | 14 | 11 | 25 | 12 | 9 | 21 |
| 3D | $V_2O_5$/$Sb_2O_2$/$TiO_2$ | 1.5 | 400 | 87 | 24 | 3 | 27 | 21 | 3 | 24 |
|    |    | 2.6 |     | 65 | 16 | 4 | 20 | 11 | 2 | 13 |
|    |    | 4.1 |     | 63 | 12 | 3 | 15 | 8  | 2 | 10 |
| 3E | PVMo/$SiO_2$ | 1.5 | 390 | 85 | 19 | 5 | 24 | 16 | 5 | 21 |
|    |    | 2.6 |     | 98 | 3  | 5 | 8  | 3  | 4 | 7  |
|    |    | 4.1 |     | 99 | 0  | 0 | 0  | 0  | 0 | 0  |
| 3F | VPO | 1.5 | 425 | 46 | 9  | 0 | 9  | 4  | 0 | 4  |
|    |    | 2.5 |     | 36 | 12 | 0 | 12 | 4  | 0 | 4  |
|    |    | 4.1 |     | 29 | 14 | 0 | 14 | 4  | 0 | 4  |
| 3G | $V_2O_5$/LTL | 1.5 | 430 | 100 | 26 | 5 | 31 | 26 | 5 | 31 |
|    |    | 2.6 |     | 100 | 6  | 4 | 10 | 6  | 4 | 10 |
|    |    | 4.1 |     | 100 | 30 | 7 | 40 | 30 | 7 | 37 |
| 3H | $V_2O_5$/hydrotalc. | 1.5 | 425 | 98 | 30 | 5 | 35 | 29 | 5 | 34 |
|    |    | 2.5 |     | 98 | 26 | 6 | 32 | 25 | 6 | 31 |
|    |    | 4.0 |     | 95 | 26 | 5 | 31 | 25 | 5 | 30 |
| 3I | $V_2O_5$/$CeO_2$ | 0.8 | 400 | 94 | 13 | 4 | 19 | 12 | 4 | 16 |
|    |    | 1.8 |     | 90 | 12 | 4 | 16 | 11 | 3 | 14 |
|    |    | 2.8 |     | 86 | 11 | 3 | 14 | 10 | 3 | 12 |
| 3J | $V_2O_5$/$La_2O_3$ | 0.9 | 400 | 91 | 15 | 0 | 15 | 14 | 0 | 14 |
|    |    | 1.9 |     | 79 | 16 | 1 | 16 | 13 | 1 | 14 |
|    |    | 2.9 |     | 86 | 16 | 0 | 16 | 13 | 0 | 13 |

TABLE 2

Catalyst = $V_2O_5$/MOEC; Bed Vol. = 8 mL;
Particle Size = 0.25–0.50 mm
Liquid Feed = 50% w/w 2-MePDA in $H_2O$

| Ex | HOS | $NH_3$/org | Air/org | CT/sec | T/°C. | X | $S^{β-pic}$ | $S^{3-CN}$ | $S^{Tot}$ | $Y^{β-pic}$ | $Y^{3-CN}$ | $Y^{Tot}$ |
|---|---|---|---|---|---|---|---|---|---|---|---|---|
| 3K | 0.9 | 5.3 | 15 | 1.5 | 413 | 99 | 19 | 16 | 35 | 19 | 16 | 35 |
|    | 1.9 | 5.0 | 15 | 1.5 | 420 | 100 | 20 | 16 | 36 | 20 | 16 | 36 |
|    | 2.9 | 4.7 | 15 | 1.5 | 419 | 100 | 19 | 15 | 34 | 19 | 15 | 34 |
| 3L | 0.9 | 7.5 | 27 | 2.0 | 414 | 99 | 11 | 24 | 35 | 11 | 24 | 35 |
|    | 1.9 | 7.2 | 27 | 2.1 | 413 | 100 | 9.0 | 24 | 31 | 9.0 | 24 | 33 |
|    | 2.9 | 7.5 | 27 | 2.0 | 415 | 100 | 7.6 | 25 | 32 | 7.6 | 25 | 32 |
| 3M | 0.9 | 5.0 | 5.3 | 1.0 | 439 | 100 | 11 | 17 | 28 | 11 | 17 | 28 |
|    | 1.9 | 4.2 | 5.3 | 1.0 | 425 | 100 | 10 | 14 | 24 | 10 | 14 | 24 |
|    | 2.9 | 5.0 | 5.2 | 1.0 | 436 | 100 | 14 | 17 | 31 | 14 | 17 | 31 |
| 3N | 0.9 | 8.5 | 27 | 2.1 | 396 | 100 | 1.9 | 33 | 35 | 1.9 | 33 | 35 |
|    | 1.9 | 8.5 | 27 | 2.1 | 393 | 100 | 4.8 | 31 | 36 | 4.8 | 31 | 36 |
|    | 2.9 | 8.2 | 27 | 2.1 | 393 | 100 | 10 | 28 | 38 | 10 | 28 | 38 |
| 3O | 1.0 | 13 | 28 | 2.9 | 394 | 100 | 0.1 | 39 | 39 | 0.1 | 39 | 39 |

TABLE 2-continued

Catalyst = $V_2O_5$/MOEC; Bed Vol. = 8 mL;
Particle Size = 0.25–0.50 mm
Liquid Feed = 50% w/w 2-MePDA in $H_2O$

| Ex | HOS | $NH_3$/org | Air/org | CT/sec | T/°C. | X | $S^{\beta\text{-pic}}$ | $S^{3\text{-CN}}$ | $S^{Tot}$ | $Y^{\beta\text{-pic}}$ | $Y^{3\text{-CN}}$ | $Y^{Tot}$ |
|---|---|---|---|---|---|---|---|---|---|---|---|---|
|  | 2.0 | 13 | 28 | 2.9 | 390 | 100 | 0.1 | 40 | 40 | 0.1 | 40 | 40 |
|  | 3.0 | 13 | 28 | 2.9 | 390 | 100 | 0.1 | 38 | 38 | 0.1 | 38 | 38 |
| 3P | 0.9 | 14 | 29 | 2.8 | 374 | 100 | 3.9 | 34 | 38 | 3.9 | 34 | 38 |
|  | 1.9 | 14 | 29 | 2.8 | 376 | 100 | 7.6 | 25 | 33 | 7.6 | 25 | 33 |
|  | 2.9 | 14 | 22 | 3.3 | 377 | 100 | 14 | 20 | 34 | 14 | 20 | 34 |
| 3Q | 0.9 | 17 | 29 | 2.1 | 392 | 100 | 0.4 | 37 | 37 | 0.4 | 37 | 37 |
|  | 1.9 | 18 | 25 | 2.3 | 394 | 100 | 2.5 | 38 | 41 | 2.5 | 38 | 41 |
|  | 2.9 | 18 | 25 | 2.2 | 401 | 100 | 3.9 | 30 | 34 | 3.9 | 30 | 34 |
| 3R | 0.7 | 9.4 | 12 | 3.5 | 554 | 100 | 23 | 1 | 24 | 23 | 1 | 24 |
|  | 1.6 | 9.4 | 12 | 2.3 | 555 | 100 | 16 | 2 | 18 | 16 | 2 | 18 |

EXAMPLE 4

Comparison of 3-CN Production from 2-MePDA and 2-Methylglutaronitrile

The results shown in Table 3 were obtained using a catalyst containing 10% w/w $V_2O_5$ on a $SiO_2$—$Al_2O_3$ support (about 45% w/w $Al_2O_3$) in the fixed bed microreactor described above. The catalyst was bound with $SiO_2$ (20% w/w, Ludox AS-40) and following drying (80° C.) and calcination (550° C. for 6 hours) was crushed and sieved to give 0.25–0.50 mm particles. As shown, processes of the invention employing 2-MePDA achieve much higher yields of 3-cyanopyridine than those obtained using 2-MGN as a starting material.

the catalyst was initiated by passing air through a distributor plate at the base of the reactor. Electric heating was applied to the reactor to achieve the desired operating temperature (400–425° C.). Gaseous ammonia was then metered (rotometer) into a feed vaporization zone followed by the 2-MePDA containing liquid feed (peristaltic pump). The mixed ammonia and 2-MePDA stream were then fed to the reactor via a sparger tube. The $NH_3$/organic and air/organic molar ratios were adjusted to give a reactor superficial velocity of about 0.3 m/second in all runs.

The reactor effluent was passed through a filter head before being condensed in a counter-current flow of distilled water percolating over stainless steel Raschig rings. The recovered liquid from the first hour of operation was discarded before a one-hour test period was commenced. The

TABLE 3

| Ex | Feed | HOS | T/° C. | CT/sec | $H_2O$/org | $NH_3$/org | Air/org | X | $S^{3\text{-CN}}$ | $Y^{3\text{-CN}}$ |
|---|---|---|---|---|---|---|---|---|---|---|
| 4A | MGN | 1.0 | 390 | 2.4 | — | 6.2 | 24 | 97 | 0.5 | 0.5 |
|  |  | 2.0 |  |  |  |  |  | 95 | 0.4 | 0.4 |
|  |  | 2.9 |  |  |  |  |  | 95 | 0.4 | 0.4 |
| 4B | MGN-$H_2O$ | 0.8 | 400 | 1.9 | 6.3 | 6.4 | 25 | 95 | 0.4 | 0.4 |
|  |  | 1.9 |  |  |  |  |  | 96 | 0.4 | 0.4 |
| 4C | 2-MePDA-$H_2O$ | 0.9 | 391 | 2.9 | 6.5 | 13 | 28 | 100 | 39 | 39 |
|  |  | 1.9 |  |  |  |  |  | 100 | 40 | 40 |
|  |  | 2.9 |  |  |  |  |  | 100 | 38 | 38 |
| 4D | 2-MePDA-3-MePip | 0.9 | 400 | 2.0 | — | 7.2 | 29 | 99 | 42 | 42 |
|  |  | 1.9 |  |  |  |  |  | 99 | 43 | 42 |
|  |  | 2.9 |  |  |  |  |  | 99 | 42 | 41 |

EXAMPLE 5

Fluid-bed Reactions

A series of runs was performed in a fluidized bed reactor. The powder form of the $V_2O_5$/MOEC catalyst (705 gm) was loaded into a 4.1 cm I.D. fluid-bed reactor. Fluidization of recovered product was weighed and analyzed by gas chromatography using a similar procedure described above for the fixed-bed reactor. In all cases, the conversion of 2-MePDA was found to be at least 99.5%. The results, shown in Table 4, confirm that 3-CN can also be formed from 2-MePDA in a fluid-bed reactor.

TABLE 4

| Ex | % wt $H_2O$ | HOS | $NH_3$/org | Air/org | CT/sec | T/°C. | $S^{\beta\text{-pic}}$ | $S^{3\text{-N}}$ | $S^{Tot}$ | $Y^{\beta\text{-pic}}$ | $Y^{3\text{-CN}}$ | $Y^{Tot}$ |
|---|---|---|---|---|---|---|---|---|---|---|---|---|
| 5A | 50 | 1.8 | 9.5 | 39 | 3.2 | 400 | 0 | 19 | 19 | 0 | 19 | 19 |
| 5B | 50 | 1.5 | 6.5 | 35 | 3.5 | 400 | 4 | 29 | 33 | 4 | 29 | 33 |
| 5C | 50 | 1.5 | 6.4 | 34 | 3.4 | 425 | 2 | 32 | 34 | 2 | 32 | 34 |
| 5D | 0 | 1.5 | 6.0 | 34 | 3.8 | 400 | 7 | 30 | 37 | 7 | 30 | 37 |
| 5E | 0 | 1.5 | 4.2 | 24 | 3.8 | 401 | 30 | 18 | 48 | 30 | 18 | 48 |

TABLE 4-continued

| Ex | % wt H₂O | HOS | NH₃/ org | Air/ org | CT/sec | T/°C. | S$^{\beta\text{-pic}}$ | S$^{3\text{-N}}$ | S$^{Tot}$ | Y$^{\beta\text{-pic}}$ | Y$^{3\text{-CN}}$ | Y$^{Tot}$ |
|---|---|---|---|---|---|---|---|---|---|---|---|---|
| 5F | 0 | 1.5 | 4.2 | 24 | 3.7 | 425 | 26 | 23 | 49 | 26 | 23 | 49 |
| 5G | 0 | 1.5 | 1.0 | 24 | 3.7 | 424 | 27 | 21 | 48 | 29 | 21 | 48 |
| 5H | 0 | 1.5 | 1.0 | 24 | 4.1 | 454 | 26 | 21 | 47 | 26 | 21 | 47 |

While the invention has been illustrated in connection with the foregoing detailed description, it will be understood that only the preferred embodiments have been shown and that all modifications within the spirit and scope of the invention are intended to be covered. In addition, all references cited herein are indicative of the skills possessed by those practiced in the art and are hereby incorporated by reference in their entirety as if each was individually incorporated by reference and fully set forth.

What is claimed is:

1. A process for the production of 3-cyanopyridine comprising the step of ammoxidizing 2-methyl-1,5-pentanediamine to form 3-cyanopyridine.

2. The process of claim 1 wherein said ammoxidizing comprises ammoxidizing a mixture containing 2-methyl-1,5-pentanediamine and 3-methylpiperidine to form 3-cyanopyridine.

3. The process of claim 2 which comprises conducting said ammoxidizing in a fluid-bed reactor.

4. The process of claim 1 which comprises conducting said ammoxidizing in the presence of a supported metal or metal oxide catalyst.

5. The process of claim 1 which comprises conducting said ammoxidizing in the presence of a catalyst comprising an oxide of vanadium.

6. The process of claim 4 additionally comprising the steps of separating and recovering the 3-cyanopyridine after said ammoxidizing.

7. The process of claim 1 wherein:
said ammoxidizing comprises passing a vaporized feed stream containing oxygen, ammonia and 2-methyl-1,5-pentanediamine through a heated catalyst bed at a temperature of about 300° C. to about 500° C., said process also comprising condensing a product stream exiting the catalyst bed and isolating the 3-cyanopyridine product from the condensed product stream.

8. The process of claim 7 wherein said ammoxidizing comprises passing a vaporized feed stream containing oxygen, ammonia and 2-methyl-1,5-pentanediamine through a heated catalyst bed at a temperature of about 350° C. to about 450° C.

9. The process of claim 8 wherein said ammoxidizing comprises passing a vaporized feed stream containing oxygen, ammonia and 2-methyl-1,5-pentanediamine through a heated catalyst bed at a temperature of about 400° C.

10. The process of claim 7 wherein said passing comprises passing a vaporized feed stream in which the ammonia is present in a molar ratio of at least about 1:1 relative to organic in the feed stream.

11. The process of claim 10 wherein said passing includes passing said vaporized feed stream through said heated catalyst bed so as to provide a contact time of less than about 10 seconds.

12. The process of claim 11 wherein said passing comprises passing a vaporized feed stream containing said oxygen, said ammonia, said 2-methyl-1,5-pentanediamine, and 3-methylpiperidine.

13. The process of claim 12 which comprises providing an oxide of vanadium in said heated catalyst bed during said passing.

14. The process of claim 13 wherein said providing an oxide of vanadium comprises providing an oxide of vanadium on a suitable support.

15. The process of claim 14 wherein said providing an oxide of vanadium comprises providing an oxide of vanadium on a silica-alumina support.

16. The process of claim 1, wherein said ammoxidizing comprises conducting an oxidative ammonolysis process to convert said 2-methyl-1,5-pentanediamine to said 3-cyanopyridine.

17. A process of claim 1, wherein said ammoxidizing comprises passing a vaporized feed stream containing oxygen, ammonia and 2-methyl-1,5-pentanediamine through a heated catalyst bed containing an oxide of vanadium for a contact time of about 30 seconds or less and at a temperature of about 300° C. to about 500° C. to form a product stream containing 3-cyanopyridine, said process also comprising condensing the product stream exiting the catalyst bed and isolating the 3-cyanopyridine product from the condensed product stream.

18. A process of claim 17, wherein said passing comprises passing said vaporized feed stream through said heated catalyst bed at a temperature of about 350° C. to about 450° C.

19. The process of claim 17 wherein said passing includes passing said vaporized feed stream through said heated catalyst bed so as to provide a contact time of less than about 10 seconds.

20. The process of claim 1, wherein said ammoxidizing comprises passing a vaporized feed stream containing ammonia and 2-methyl-1,5-pentanediamine through a heated, oxygenated catalyst bed at a temperature of about 300° C. to about 500° C. so as to form a product stream including 3-cyanopyridine.

21. The process of claim 20, also comprising contacting said catalyst bed with gaseous oxygen so as to regenerate said catalyst bed after said passing.

22. The process of claim 21, also comprising condensing the product stream exiting the catalyst bed and isolating the 3-cyanopyridine product from the condensed product stream.

23. The process of claim 22 which comprises providing an oxide of vanadium in said catalyst bed during said passing.

24. The process of 23 wherein said providing an oxide of vanadium comprises providing an oxide of vanadium on a support.

25. The process of 23 wherein said providing an oxide of vanadium comprises providing an oxide of vanadium on a silica-alumina support.

* * * * *